United States Patent
Hause

(10) Patent No.: US 7,860,575 B2
(45) Date of Patent: Dec. 28, 2010

(54) HIGH-SIDE CURRENT REGULATOR AND METHODS FOR IMPLEMENTING A MULTIPLE CHANNEL IONTOPHORETIC DEVICE

(75) Inventor: Robert F. Hause, Bountiful, UT (US)

(73) Assignee: Encore Medical Asset Corporation, Henderson, NV (US)

( * ) Notice: Subject to any disclaimer, the term of this patent is extended or adjusted under 35 U.S.C. 154(b) by 506 days.

(21) Appl. No.: 11/429,747

(22) Filed: May 8, 2006

(65) Prior Publication Data
US 2007/0260169 A1    Nov. 8, 2007

(51) Int. Cl.
*A61N 1/08* (2006.01)
(52) U.S. Cl. ............................. 607/66; 607/2
(58) Field of Classification Search ........... 604/20, 604/501; 607/2, 66, 148
See application file for complete search history.

(56) References Cited
U.S. PATENT DOCUMENTS

| 4,019,510 A | * | 4/1977 | Ellis ........................... 604/20 |
|---|---|---|---|
| 5,169,384 A | * | 12/1992 | Bosniak et al. ............... 604/20 |
| 5,189,307 A | | 2/1993 | Fabian |
| 5,254,081 A | * | 10/1993 | Maurer et al. ................. 604/20 |
| 5,283,441 A | | 2/1994 | Fabian |
| 5,310,403 A | * | 5/1994 | Haynes ........................ 604/20 |
| 5,431,625 A | | 7/1995 | Fabian et al. |
| 6,009,344 A | * | 12/1999 | Flower et al. ................. 604/20 |

OTHER PUBLICATIONS

Dupel B.L.U.E. Electrode Set-Up Guide Brochure, Empi, Inc. Nov. 1998.
Print out of website page for Iontophor II.

* cited by examiner

*Primary Examiner*—Carl H Layno
*Assistant Examiner*—Pamela M Bays
(74) *Attorney, Agent, or Firm*—Ropes & Gray LLP

(57) ABSTRACT

Multiple channel iontophoretic devices including multiple regulators, each of which are coupled to an associated electrode. A regulated current flows through each regulator in response to a control signal. The control signal is responsive to feedback indicative of current flowing through more than one of the multiple regulators.

32 Claims, 15 Drawing Sheets

| CONFIGURATION | POSITIVE ELECTRONIC REGULATED CHANNELS | POSITIVE VIRTUAL REGULATED CHANNEL | POSITIVE UNREGULATED CHANNELS | NEGATIVE ELECTRONIC REGULATED CHANNELS | NEGATIVE VIRTUAL REGULATED CHANNEL | NEGATIVE UNREGULATED CHANNELS |
|---|---|---|---|---|---|---|
| POSITIVE ONLY | >1 | 0 | 0 | 0 | 1 NOTE 1 | >1 NOTE 1 |
| NEGATIVE ONLY | 0 | 1 NOTE 1 | >1 NOTE 1 | >1 | 0 | 0 |

Fig. 10

| CONFIGURATION | POSITIVE ELECTRONIC REGULATED CHANNELS | POSITIVE VIRTUAL REGULATED CHANNEL | POSITIVE UNREGULATED CHANNELS | NEGATIVE ELECTRONIC REGULATED CHANNELS | NEGATIVE VIRTUAL REGULATED CHANNEL | NEGATIVE UNREGULATED CHANNELS |
|---|---|---|---|---|---|---|
| POSITIVE OPERATION | >1 | 0 | 0 | 0 | 1 NOTE 1 | >1 NOTE 1 |
| NEGATIVE OPERATION | 0 | 1 NOTE 2 | >1 NOTE 2 | >1 | 0 | 0 |

Fig. 11

|  | POSITIVE ELECTRONIC REGULATED CHANNELS | POSITIVE VIRTUAL REGULATED CHANNEL | POSITIVE UNREGULATED CHANNELS | NEGATIVE ELECTRONIC REGULATED CHANNELS | NEGATIVE VIRTUAL REGULATED CHANNEL | NEGATIVE UNREGULATED CHANNELS |
|---|---|---|---|---|---|---|
|  | >0 | 0 | 0 | >0 | 1 NOTE 3 | >1 NOTE 3 |

Fig. 12

| | POSITIVE ELECTRONIC REGULATED CHANNELS | POSITIVE VIRTUAL REGULATED CHANNEL | POSITIVE UNREGULATED CHANNELS | NEGATIVE ELECTRONIC REGULATED CHANNELS | NEGATIVE VIRTUAL REGULATED CHANNEL | NEGATIVE UNREGULATED CHANNELS |
|---|---|---|---|---|---|---|
| | >0 | 1 NOTE 4 | >1 NOTE 4 | >0 | 0 | 0 |

HIGH-SIDE CURRENT REGULATOR AND METHODS FOR IMPLEMENTING A MULTIPLE CHANNEL IONTOPHORETIC DEVICE

FIELD OF THE INVENTION

The present invention relates to iontophoretic devices, and in particular, to a high-side current regulator and methods for implementing a multiple channel iontophoretic device.

RELATED APPLICATIONS

None.

FEDERALLY SPONSORED RESEARCH OR DEVELOPMENT

None.

BACKGROUND OF THE INVENTION

Single channel and multi-channel iontophoretic devices are known in the prior art. Turning to FIG. 1, a single channel iontophoretic controller 110 is illustrated connected in-vivo (i.e., connected to a human arm 112). Regulated current flows from the controller to the active electrode 114. The inactive electrode 116, in this example, is not utilized for drug delivery. Instead, it is used solely to provide a return path for the electrical current.

As illustrated in FIG. 1, the controller 110 includes a DC/DC converter that is used to convert the voltage from the power source to a higher voltage. A typical power source is a 9 Volt alkaline battery (e.g., MN1604).

A typical general-purpose commercial iontophoretic controller (e.g., IOMED PM700) includes a DC/DC converter that converts the finite battery voltage to a magnitude ranging from approximately 0.0 Volt to 70.0 Volts. The value within this range is dependent on skin resistance and current. The DC/DC converter is optional, for example some low voltage application-specific commercial iontophoretic controllers do not require, and therefore do not employ a DC/DC converter. Therefore, as used herein, the term "current regulator" shall mean either a current regulator working in conjunction with a DC/DC converter or working in conjunction with a different type of power supply that does not employ a DC/DC converter (e.g., a simple unregulated battery source power supply).

In FIG. 1, the microcontroller interfaces bi-directionally with the current regulator. In other words the microcontroller controls and monitors the current regulator. The feedback (i.e., the monitoring) is required to regulate the current if the closed-loop regulation is partly or fully controlled by the microcontroller. It is also required to verify the correct operation of the current regulator. Parameters that are measured include current and voltage. From these basic parameters additional parameters can be calculated. For example the IOMED PM700 Phoresor, which was manufactured and distributed by IOMED from 1990 to 1997. Although this device is no longer manufactured, the description provided herein also applies to PM700 successors (i.e., PM800 and PM850) and related devices (e.g., PM900). The circuitry of the PM700 measures iontophoretic current and iontophoretic output voltage. From these two basic parameters at least two additional parameters are calculated: di/dt (i.e., the rate of change of the current with respect to time) and iontophoretic dose (i.e., the integral of current with respect to time, i.e., milliAmp-minutes, i.e., charge). The monitoring of voltage, current, and the rate of change in current, is desired from both a functional and safety standpoint.

Dose is monitored as required to either display the dose (e.g., on a LCD) and/or to terminate the treatment after a finite magnitude of dose (charge) is accumulated. Voltage is monitored to verify that the iontophoretic resistance is within limits. If the resistance is too high for a given iontophoretic current setting, then the PM700 alerts the user via a "Resistance Limit" warning. If the rate of change of the current is too excessive, then the PM700 disables the iontophoretic current and issues an "Electrode Reject" error. If the measured current (i.e., "feedback") significantly deviates from the desired current (i.e., from the "command signal"), then the PM7000 disables the iontophoretic current and issues an "Electrode Reject" error.

Turning to FIG. 2, a single channel iontophoretic controller 210 is connected to two active electrodes 214A, 214B via a bifurcated cable assembly. The controller in this illustration is an Iontorhor-PM. This is a commercial iontophoretic controller than has been manufactured and sold in the United States for several years. The Iontophor-PM bifurcated cable assembly has also been manufactured and sold for several years.

The feature of utilizing a bifurcated cable assembly to provide two channels of current from a single channel device is not limited to the Iontophoretic-PM, and therefore will work with any single channel iontophoretic controller (note the equivalence of the PM700 block transformation in FIG. 1 and the block transformation of the Iontophor-PM in FIG. 2).

The bifurcated cable assembly supposedly provides approximately equal current to two body sites, thereby facilitating non-isolated multi-channel operation. However, due to differences in skin-body resistance, the two currents can deviate significantly. In addition, the two currents cannot be individually monitored. For example, if the first active electrode is improperly placed on the body, or if it is defective, or if the cable connection to this electrode is defective, then all of the current will flow through the second active electrode. As such, a bifurcated cable assembly cannot be used in any application that mandates regulated currents. More specifically the bifurcated cable assembly may be unacceptable from a functional and safely standpoint depending on the application.

Turning to FIG. 3, a block transformation of an EMPI DUPEL iontophoretic controller 310 connected in-vivo is provided wherein U.S. Pat. Nos. 5,189,307, 5,254,081, 5,283,441 and 5,431,625 are related thereto in addition to the instructions for use of the EMPI DUPEL iontophoretic controller. Part No. 360165, © 1991, 1992. Empi, Inc. In FIG. 3, the dual channel iontophoretic controller 310 is connected to two isolated pairs of electrodes. Current "I1" is isolated and totally independent from Current "I2". Because the two channels are electrically isolated, operation is analogous to utilizing two single channel iontophoretic controllers.

Turning to FIG. 4, a simplified block transformation is depicted of a device described by U.S. Pat. No. 5,310,403. As described, this iontophoretic drug delivery device 410 employs multiple open-loop current sinks and/or multiple open-loop current sources. Because the sinks, or alternatively, the sources are operated in an open-loop mode, there is no current regulation. In other words, current "I1" may deviate from current "I2." Deviation may be a result of component variation, component degradation, component failure, ambient conditions (e.g., temperature), etc. Additionally, if there is a defect in electrode construction, or in the cable assembly, the associated iontophoretic current will be incorrect or totally absent for that particular channel. Likewise, if the user incorrectly hydrates an electrode, or incorrectly adheres an electrode, or the like, then the current will be incorrect or totally absent for that particular channel. The faults that have just been described will unfortunately be tolerated by the iontophoretic device because the current in each channel are not monitored, i.e., there is no closed-loop regulation from an electronic control statepoint, and additionally there is no feedback monitoring for functionality or safety. Further, the currents in each channel cannot be independently controlled.

It is the purpose of this invention to provide a solution to many, if at not all, of the above stated problems.

SUMMARY OF THE INVENTION

The present invention is generally directed to a high-side current regulator for an iontophoretic device and methods for implementing a multiple channel iontophoretic device. According to one aspect of the invention, an iontophoretic controller is provided having a plurality of regulators paired with a plurality of active electrodes, and wherein each regulator regulates current to or from its paired active electrode.

According to another aspect of the invention, a plurality of electrodes are connected to a person. Current is then applied to the electrodes. Further, the current is regulated for each of the electrodes.

Other embodiments, systems, methods, features, and advantages of the present invention will be, or will become, apparent to one having ordinary skill in the art upon examination of the following drawings and detailed description. It is intended that all such additional systems, methods, features, and advantages included within this description be within the scope of the present invention, and be protected by the accompanying claims.

DESCRIPTION OF THE DRAWINGS

The invention may be better understood with reference to the following drawings. The components in the drawings are not necessarily to scale, emphasis instead being placed upon illustrating the principles of the invention. In the drawings, like reference numerals designate corresponding parts throughout the several views.

FIG. 10 is a table with desired characteristics of a single polarity iontophoretic controller in accordance with the present invention;

FIG. 11 is a table with desired characteristics of a dual polarity, non-simultaneous operation, iontophoretic controller in accordance with the present invention;

FIG. 12 is a table with desired characteristics of a dual polarity, simultaneous operation, iontophoretic controller in accordance with the present invention and having non-electronic negative current channel(s).

DESCRIPTION OF DETAILED EMBODIMENTS

The following descriptions of detailed embodiments are for exemplifying the principles and advantages of the inventions claimed herein. They are not to be taken in any way as limitations on the scope of the inventions.

Figure 1:
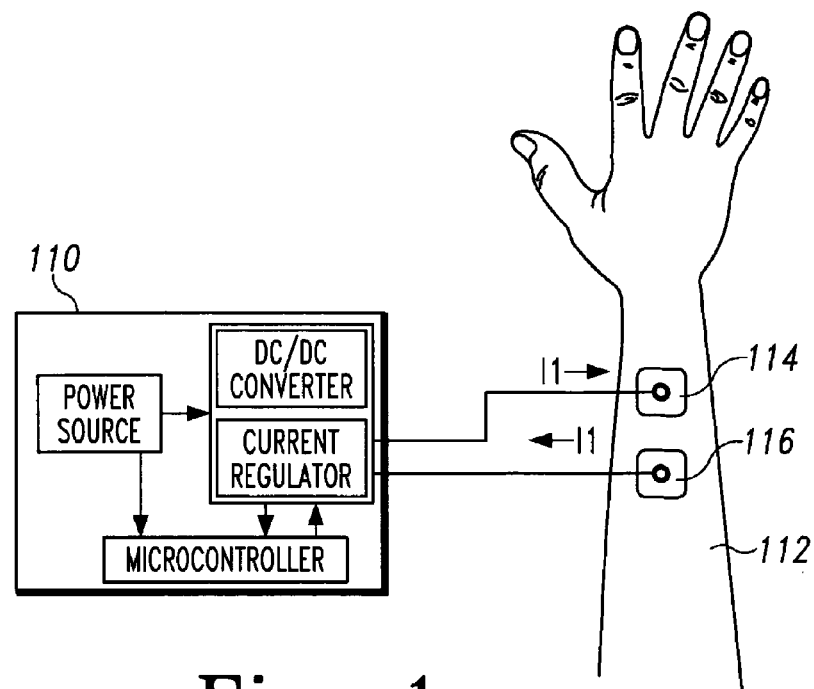
FIG. 1 (Prior Art) is a simplified block diagram of a single channel iontophoretic controller connected to a human arm.
Figure 2:
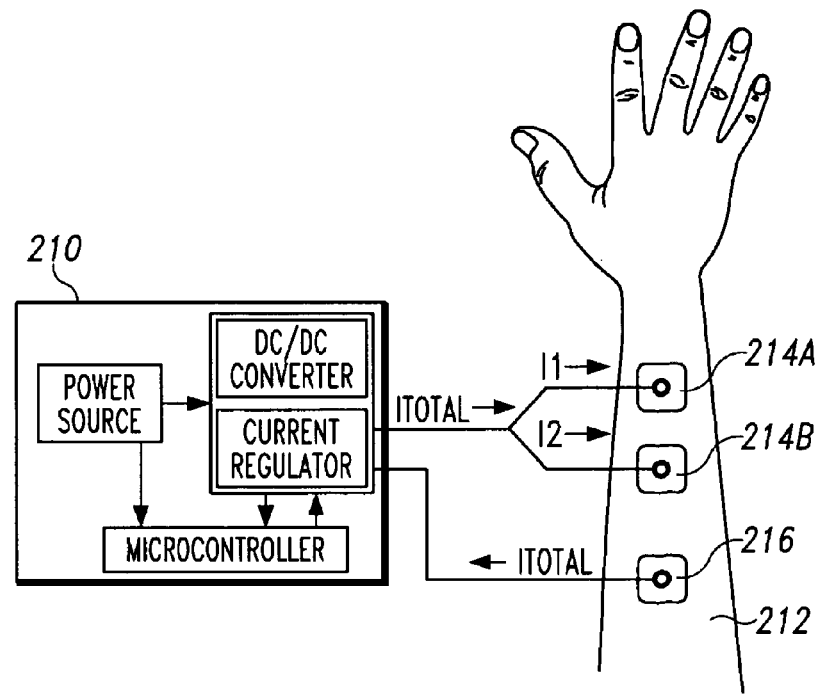
FIG. 2 (Prior Art) is a simplified block diagram of a single channel iontophoretic controller having a bifurcated cable assembly connected to a human arm.
Figure 3:
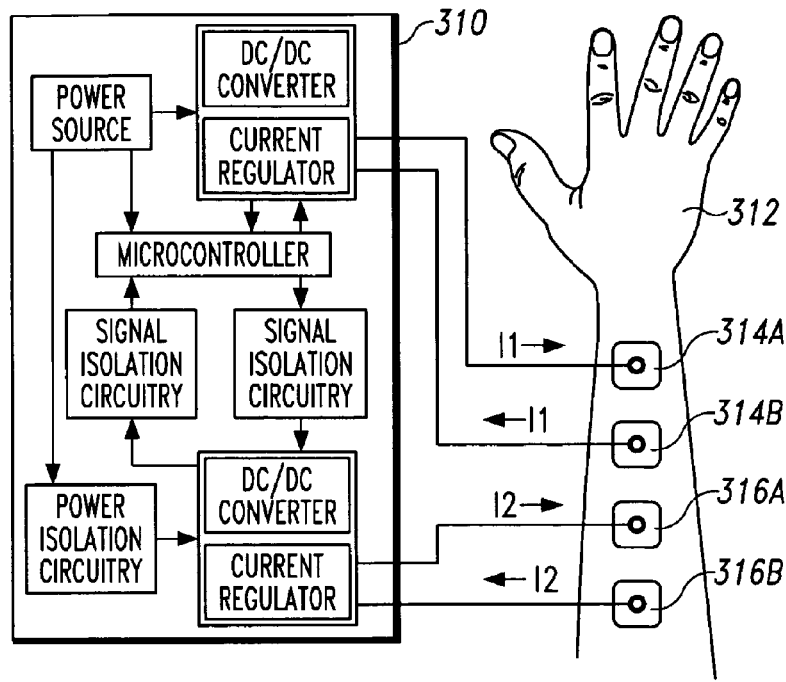
FIG. 3 (Prior Art) is a simplified block diagram of a dual channel iontophoretic controller coupled to a human arm and having isolated regulators and isolated power supplies.
Figure 4:
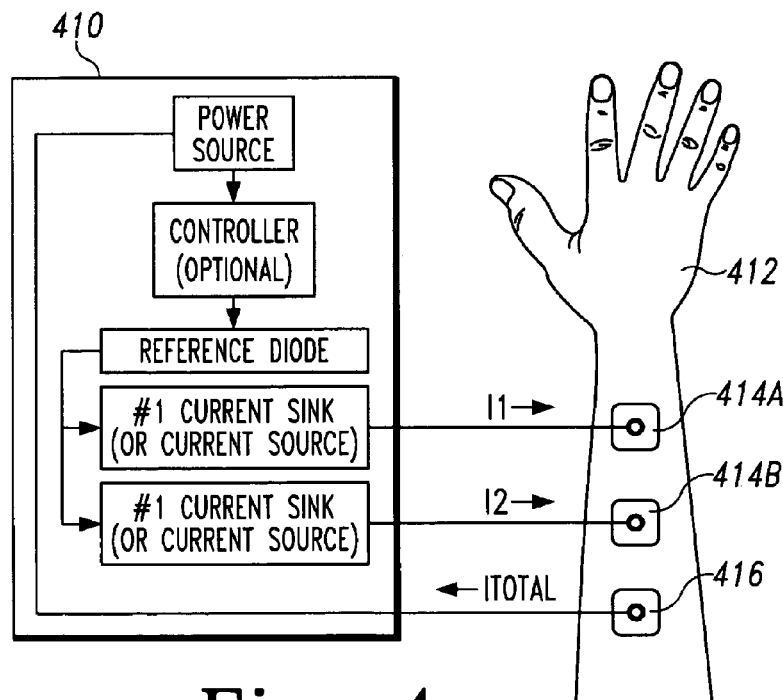
FIG. 4 (Prior Art) is a simplified block diagram of a multiple channel iontophoretic controller having an open-loop current sink and/or source.
Figure 5:
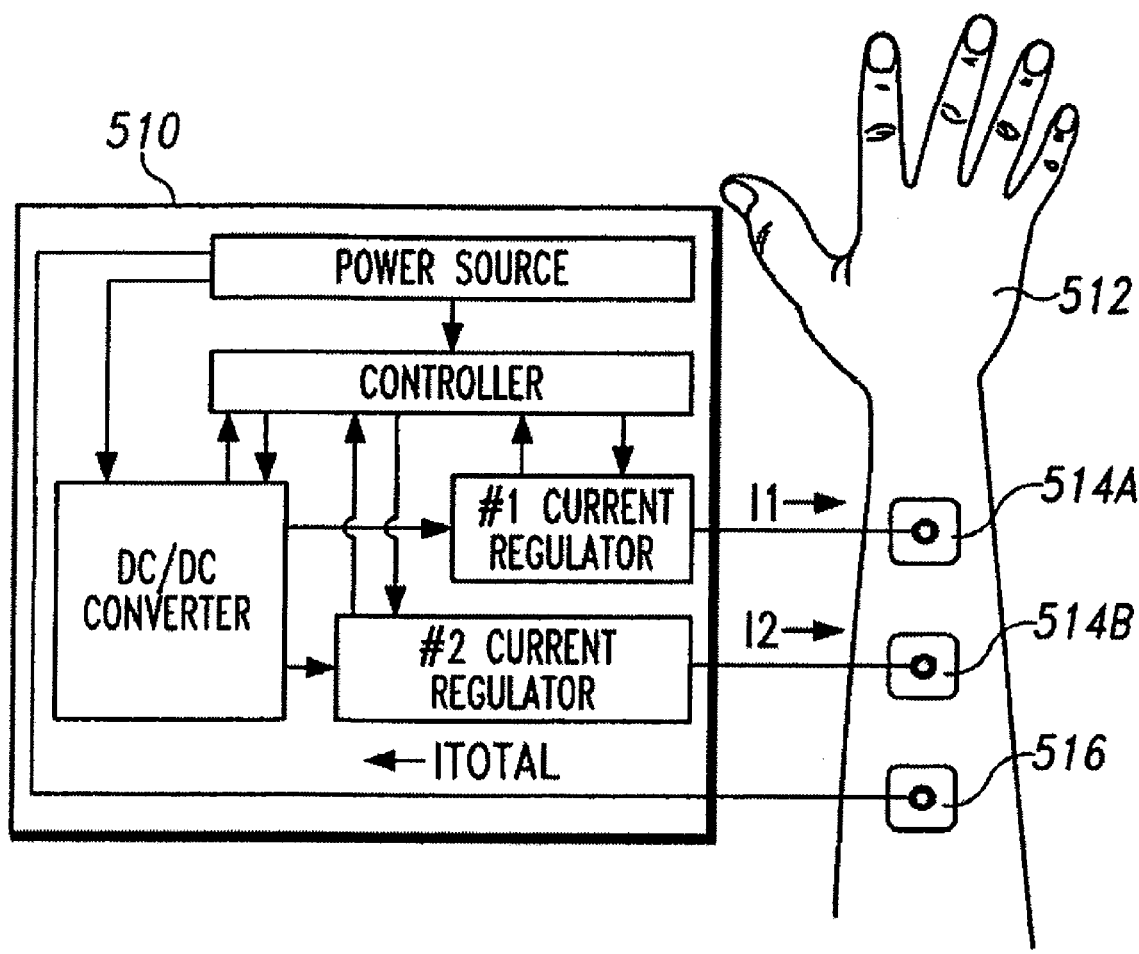
FIG. 5 is a simplified block diagram of an iontophoretic controller in accordance with the present invention and attached to a human arm.

Turning to FIG. 5, a simplified block diagram is provided of a device in accordance with the present invention wherein the device is connected in-vivo. As shown, the device 510 utilizes high-side current regulators wherein there are multiple channels and therefore multiple active electrodes. The current to each active electrode 514A, 514B is both regulated and monitored. As such, the present invention allows for the safety and functional requirements employed in present-day single channel commercial iontophoretic drug delivery controllers to be employed in a multi-channel device.

Stated another way, the present invention can be employed to create a multi-channel iontophoretic device with regulated current output for each channel. As such, the device has the capability to employ all of the safety and functional requirements found in present-day single channel commercial iontophoretic devices. Additionally, the currents for each channel are not isolated, which facilitates the use of a single inactive electrode, if desired.

As will also be appreciated by those having ordinary skill in the art, the present invention can be used to create various types of multi-channel controllers. As described herein, but not limited thereto, the present invention will be described with respect to four types of multi-channel iontophoretic controllers: 1) a device employing multiple positive polarity current regulators; 2) a device employing multiple negative polarity current regulators; 3) a device employing multiple current regulators of both polarities operating non-simultaneously; and, 4) a device employing multiple current regulators of both polarities, operating simultaneously.

The devices employing multiple channels of current regulators of both polarities will be classified herein as either operating in a non-simultaneous mode or simultaneous mode.

The non-simultaneous mode shall mean that the electronic current regulators of one polarity are enabled while those of the opposite polarity are disabled. The simultaneous mode shall mean that the electronic current regulators of each polarity are enabled and work in conjunction.

Figure 6:
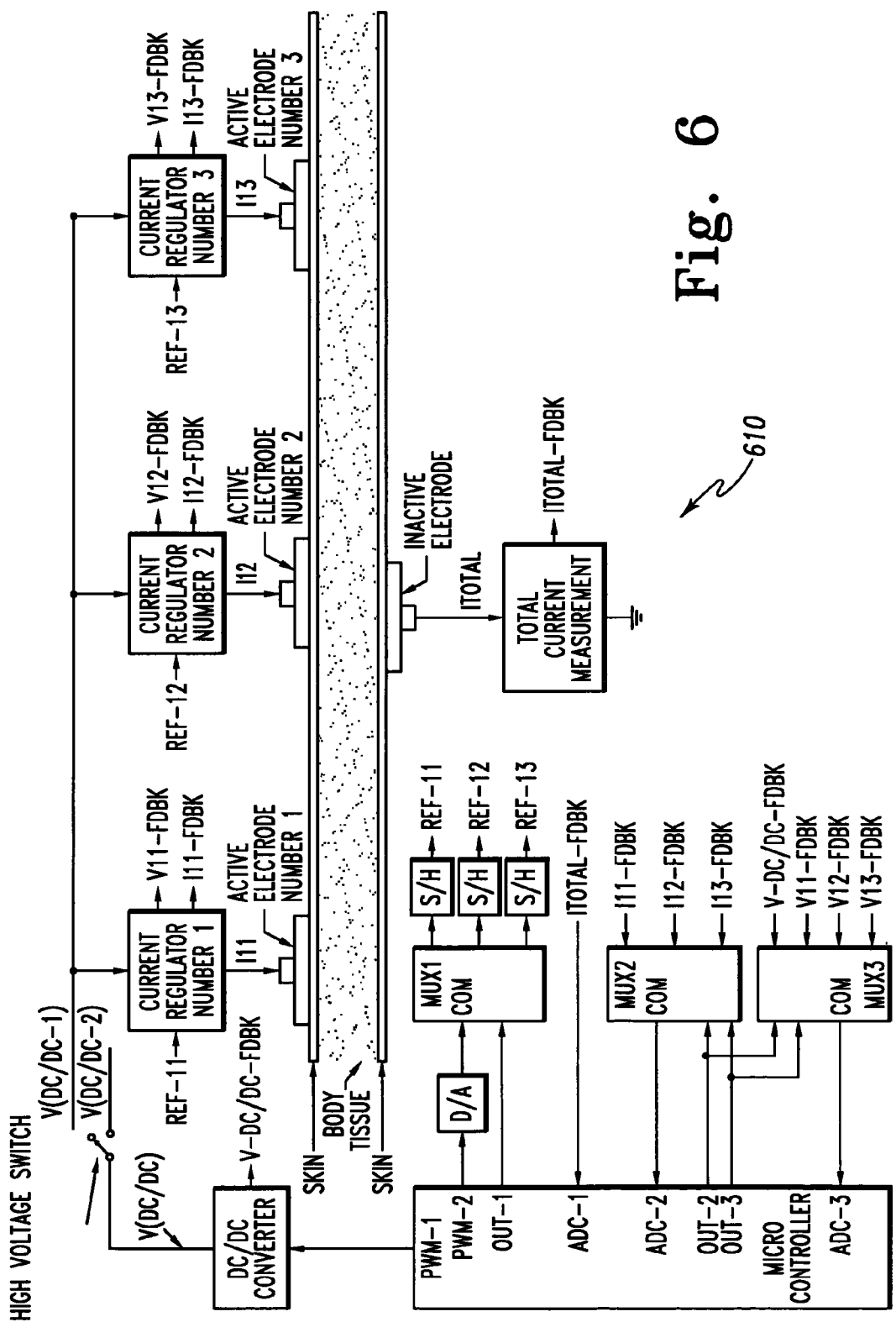
FIG. 6 is a simplified block diagram of a portion of an iontophoretic controller having multiple positive polarity current regulators.

Turning to FIG. 6, an illustration is provided on a portion of an iontophoretic controller 610 with three (i.e., with multiple) electronic positive polarity current regulators (i.e., with multiple high-side current regulators). As will be appreciated by those having ordinary skill in the art, the present invention is not limited to three electronic positive polarity current regulators; two or more electronic positive polarity current regulators may be employed. Likewise the present invention is not limited to one negative polarity current channel (i.e., one non-electronic current regulated channel), one or more negative polarity current channels may be employed. If one negative current channel is employed then this channel is classified herein as being virtually regulated (i.e., the current is the sum of the currents from the electronic positive polarity regulators, and is therefore also regulated.) If two or more negative polarity current channels are employed then the current in each channel will be unregulated.

A commercial example is an iontophoretic delivery device used in conjunction with a face electrode. The face electrode is segmented into three active electrodes and one inactive electrode (4 electrodes total). In an embodiment one active electrode (electrode 1) can be located to the left side of a patient's nose, a second electrode (electrode 2) can be located to the right side of the patient's nose, a third electrode (electrode 3) can be located on the forehead, and an inactive electrode surrounds each electrode. The iontophoretic current applied to electrodes 1 and 2 is 150 microAmps for the initial 10 minutes. The iontophoretic current applied to electrode 3 is 200 microAmps for the entire 15-minute treatment. The total iontophoretic current is the sum of the regulated currents, which are 500 microAmps for the first 10 minutes and 200 microAmps for the last 5 minutes.

In an embodiment, the controller 610 monitors the voltage required for each current regulator (e.g., V11-FDBK, V12-FDBK, and V13-FDBK) as required for functionality and safety. For instance, the magnitude of each of these voltages can be evaluated as required to automatically adjust the voltage output of the DC/DC converter proportionally.

In an embodiment, the controller 610 monitors the independent currents (I11-FDBK, I12-FDBK, and I13-FDBK) of each electronic regulator and the total current (ITOTAL-FDBK) as required for functionality and safety. In addition the current feedback can be used for full regulation (assuming digitally controlled regulations), or to supplement the control of an analog current regulator.

In another embodiment, an iontophoretic device provides relatively large current (e.g., local anesthesia prior to surgery). In this embodiment, the active electrode employs three segments (i.e., three active electrode segments). The iontophoretic current applied to two of the electrodes can be 5 milliAmps and the iontophoretic current applied to the third electrode can be 4 milliAmps. Accordingly, the total iontophoretic current is 14 milliAmps (14,000 microAmps).

In use, two discrete inactive electrodes can be used because the magnitude of the total iontophoretic current is too excessive for one inactive electrode. Preferably, the iontophoretic current returned by the two inactive electrodes is approximately equal. In an embodiment, the iontophoretic current for each of the two inactive electrodes can be monitored to verify that the total current is approximately shared. For example, a microcontroller firmware routine can be implemented to warn the user if the difference in the magnitude of iontophoretic current in each inactive electrode varies, for example, by more than 1.25 milliAmps.

In an embodiment, there can be a separate electronic current regulator for each positive polarity current channel. Each high-side regulator can be driven by an associated low-side analog command signal (e.g., REF-11, which is referenced to the power supply common rails) from the microcontroller. Each command signal is independent of the other command signals. In this embodiment, one D/A (i.e., DAC, i.e., Digital-to-Analog Converter) is used to program three S/H circuits (i.e., sample and hold circuits). Each regulator provides low-side iontophoretic current feedback and low-side output voltage feedback as required by the microcontroller, which is referenced to the power supply common rail, (i.e., is referenced to the low-side rail). As such the regulators can be fully controlled via the microcontroller (e.g., a digital control-loop), or they can be independently controlled (e.g., an analog servo that tracks an analog command signal from the microcontroller), or regulation can be accomplished via a combination analog-digital controller-loop.

The controller 610 is not limited to using a digital microcontroller. For instance, instead of a digital microcontroller, an ASIC, analog controller, or other type of control circuit can be used. The reference circuits (i.e., command signal circuits) within the controller 610 are also not limited to one D/A interfaced with multiple S/H circuits via an analog multiplexer. For example multiple D/As, or multiple digital potentiometers; or similar reference circuits can be employed.

A high voltage switch within the controller 610 can be desired in devices that employ both one or more high-side current regulators and one or more low-side current regulators, wherein only the high-side regulators or only the low-side regulators are employed at any given time. The switch position V(DC/DC-1) feeds high voltage to the high-side current regulators and switch position V(DC/Dc-2) feeds high voltage to the low-side current regulators. In applications that require high-side current regulators only, or in applications that require low-side current regulators only, or in applications that require simultaneous operation of the high-side current regulators and low-side current regulators the high voltage switch may not be required. The high voltage switch can be an elector-mechanical switch (e.g., rotary switch), elector-magnetic switch (e.g., relay), electronic switch (P-channel MOSFET or PNP bipolar transistor), or the like.

The DC/DC converter within the controller 610 can be desired in an iontophoretic device that is battery-operated with for example, a typical battery voltage of about 9 Volts. In some iontophoretic devices a power supply voltage exceeding 9 Volts is desired (e.g., the IOMED PM700 Phoresor requires 70 Volts maximum). Therefore a DC/DC converter is employed to convert the lower voltage of the battery to a higher operating voltage. In an alternative, two 9-Volt alkaline batteries are employed to provide an operating potential of 18 Volts, thereby avoiding the need for a DC/DC converter. In summary, the voltage required for a given application is primarily dependent on the resistive characteristics of the bio-membrane (e.g., human skin) through which the current will flow, and on the maximum magnitude of the current, and this voltage requirement dictates the need for a DC/DC converter. In an embodiment, each current channel or each negative current channel can be utilized in connection with either an active or inactive electrode.

Figure 7A:
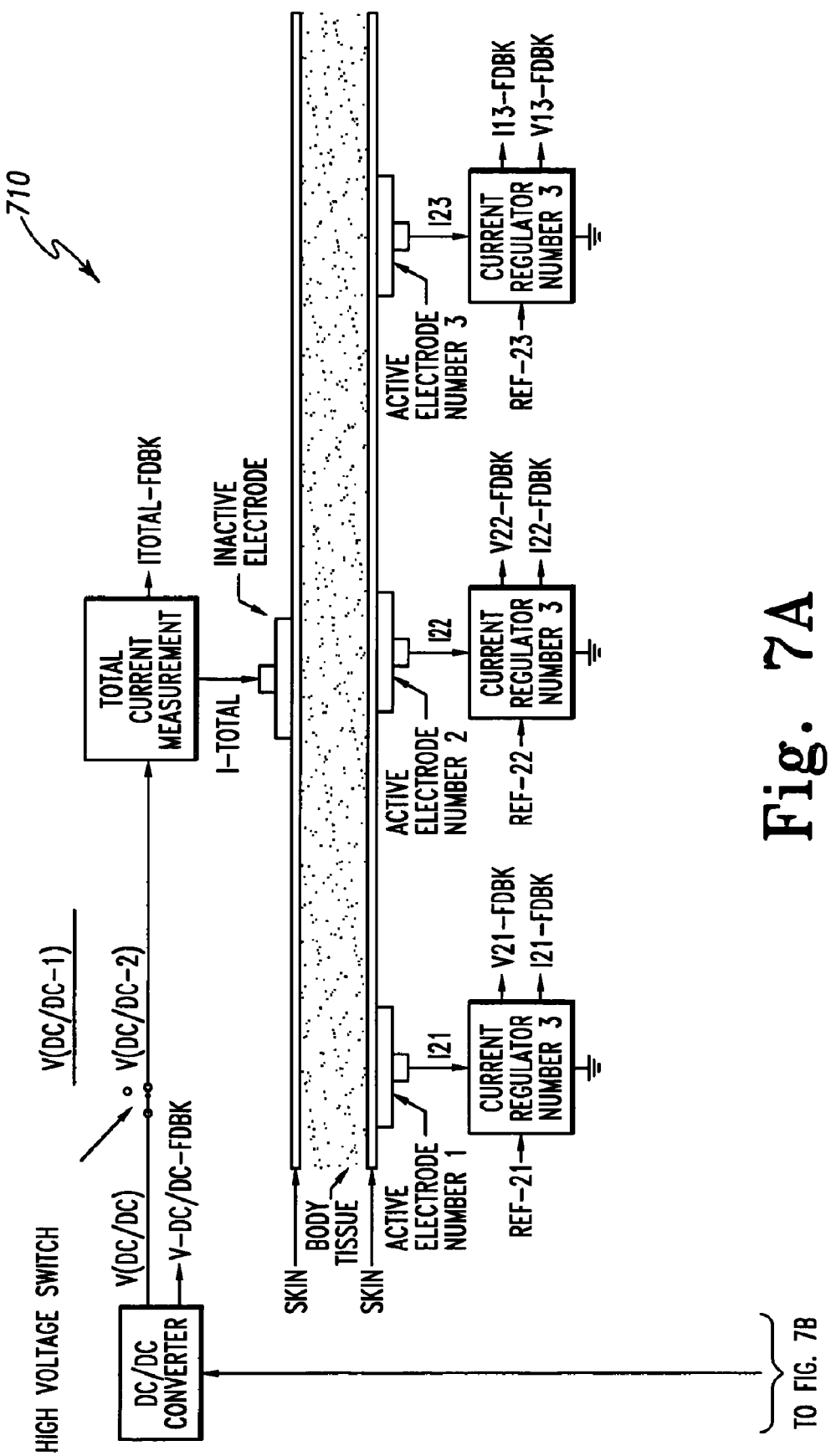
FIG. 7 is a simplified block diagram of a portion of an iontophoretic controller having multiple negative polarity current regulators.
Figure 7B:
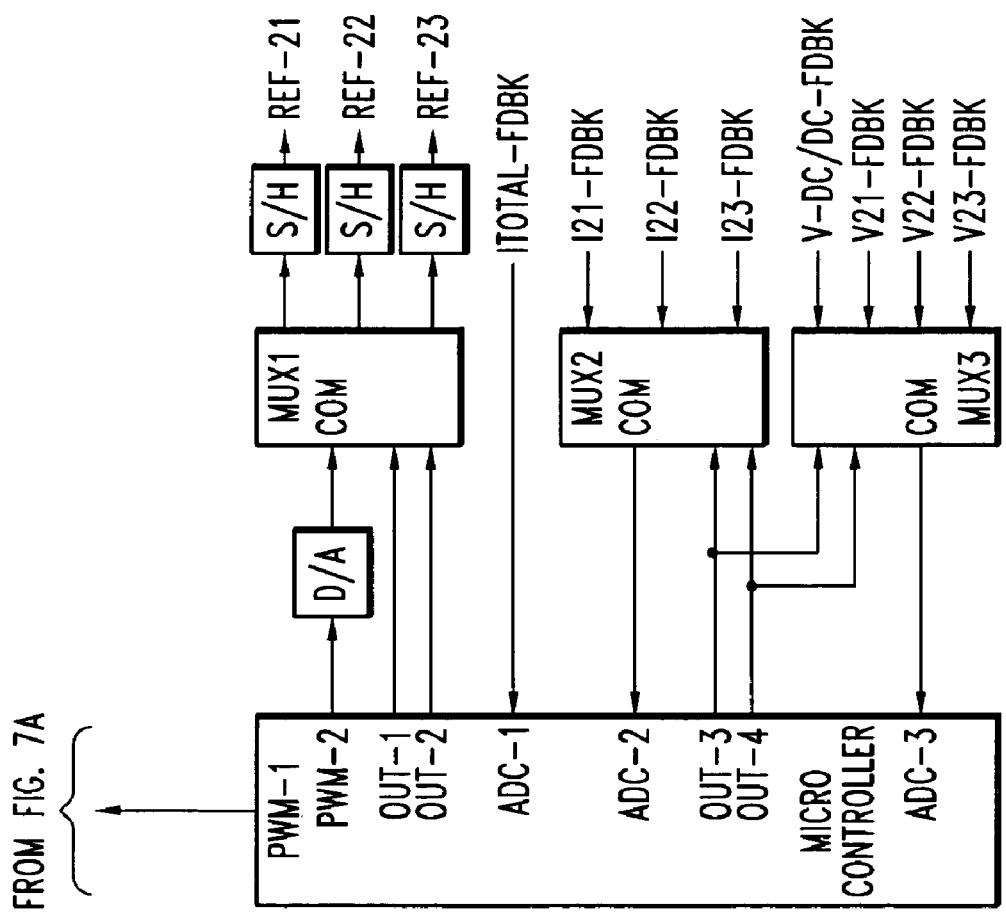

Turning to FIG. 7, an illustration is provided of a portion of an iontophoretic controller 710 with three (i.e., with multiple) negative polarity current regulators. As will be appreciated by those having ordinary skill in the art, in an alternative embodiment, more or less than three current regulators can be employed. For instance, two or more than three negative polarity current regulators may be employed. Likewise, in an alternative embodiment, more than one positive polarity current channels can be employed. If one positive current channel is employed then this channel is classified herein as being virtually regulated. If two or more positive polarity current channels are employed then the current in each channel will be unregulated.

In an embodiment, the iontophoretic current applied to each electrode is 2 milliAmps (2,000 microAmps) for 10 minutes. The total current is the sum of the regulated currents, which is 6 milliAmps for 10 minutes. A single typical dispersive electrode, which has a current carrying capacity 6 milliAmps, can be employed for the inactive electrode.

In an embodiment, the controller monitors the voltage required for each electronic regulator (V21-FDBK, V22-FDBK, and V23-FDBK) as needed for functionality and safety. The magnitude of each of these voltages can be evaluated as required to automatically adjust the voltage output of the DC/DC converter proportionally.

The controller can monitor the independent currents (I21-FDBK, I22-FDBK, and I23-FDBK) of each electronic regulator and the total current (ITOTAL-FDBK) as may be required for functionality, safety, and regulation.

Figure 8:
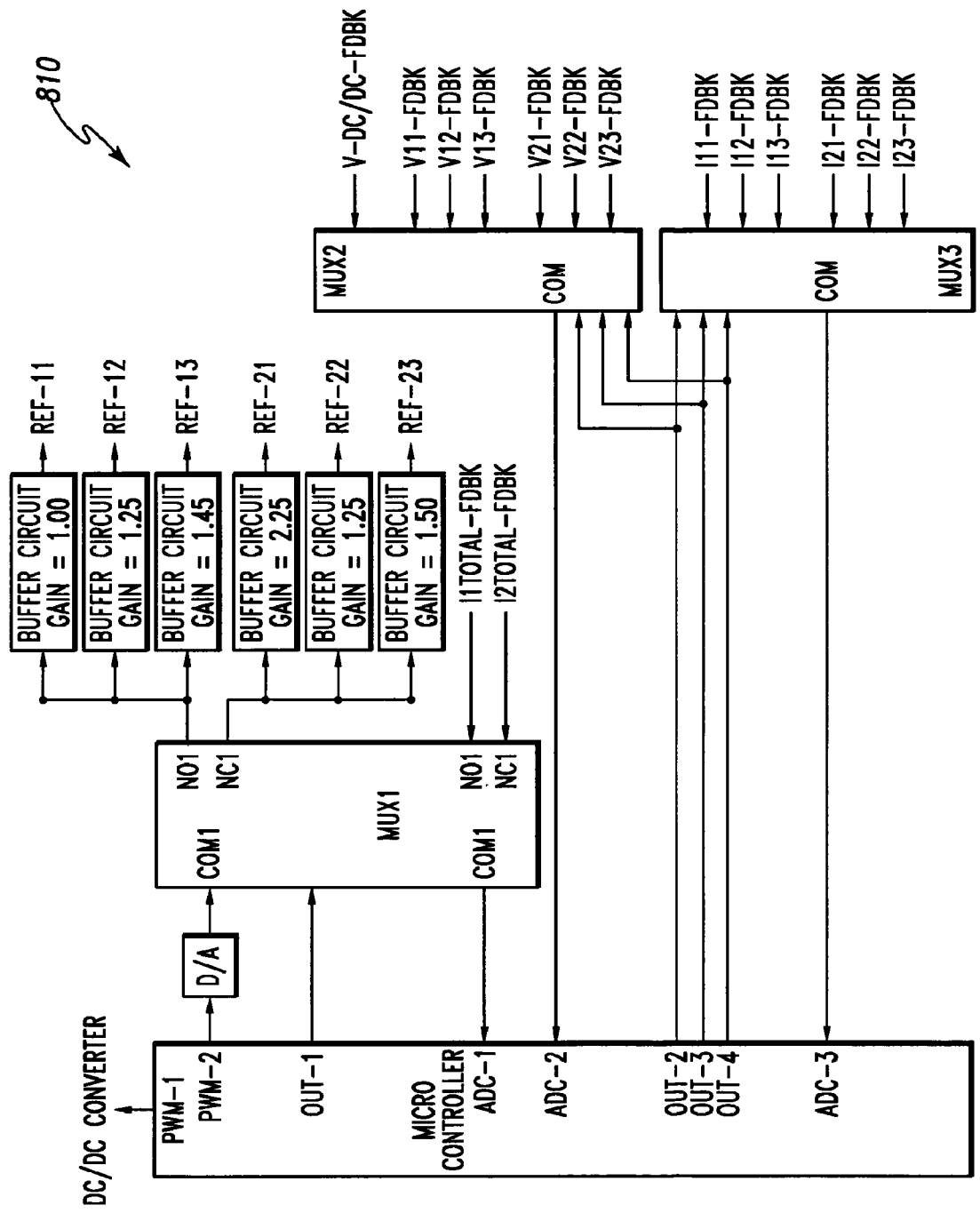
FIG. 8 is a simplified block diagram of a portion of an iontophoretic controller having non-simultaneous dual polarity operation.

In an embodiment, the controller can employ multiple electronic current regulators of positive and negative polarities. A non-simultaneous dual polarity device can be constructed to employ, for example, the circuits illustrated in FIGS. 6, 7 and 8. Turning to FIG. 8, there is illustrated reference and feedback circuits for both the high-side current regulators and low-side current regulators. Desirably, the reference and feedback circuits are only enabled for one polarity at any given time. Accordingly, MUX (i.e., Analog Multiplexer 1), MUX2, and MUX3 are used to switch the reference and feedback circuits.

Basically, as appreciated by those having ordinary skill in the art, a non-simultaneous dual polarity device functions at one particular time, as either a controller employing only multiple positive polarity current regulators, as explained previously, or as a controller employing only multiple negative polarity current regulators, as also previously explained in detail.

Because the requirements of this type of device mandate single polarity operation only, desirably the device should employ the illustrated high voltage switch or an equivalent. This switch enables only those electronic regulators and associated circuits for one polarity, or the other, at any given time.

Figure 9A:
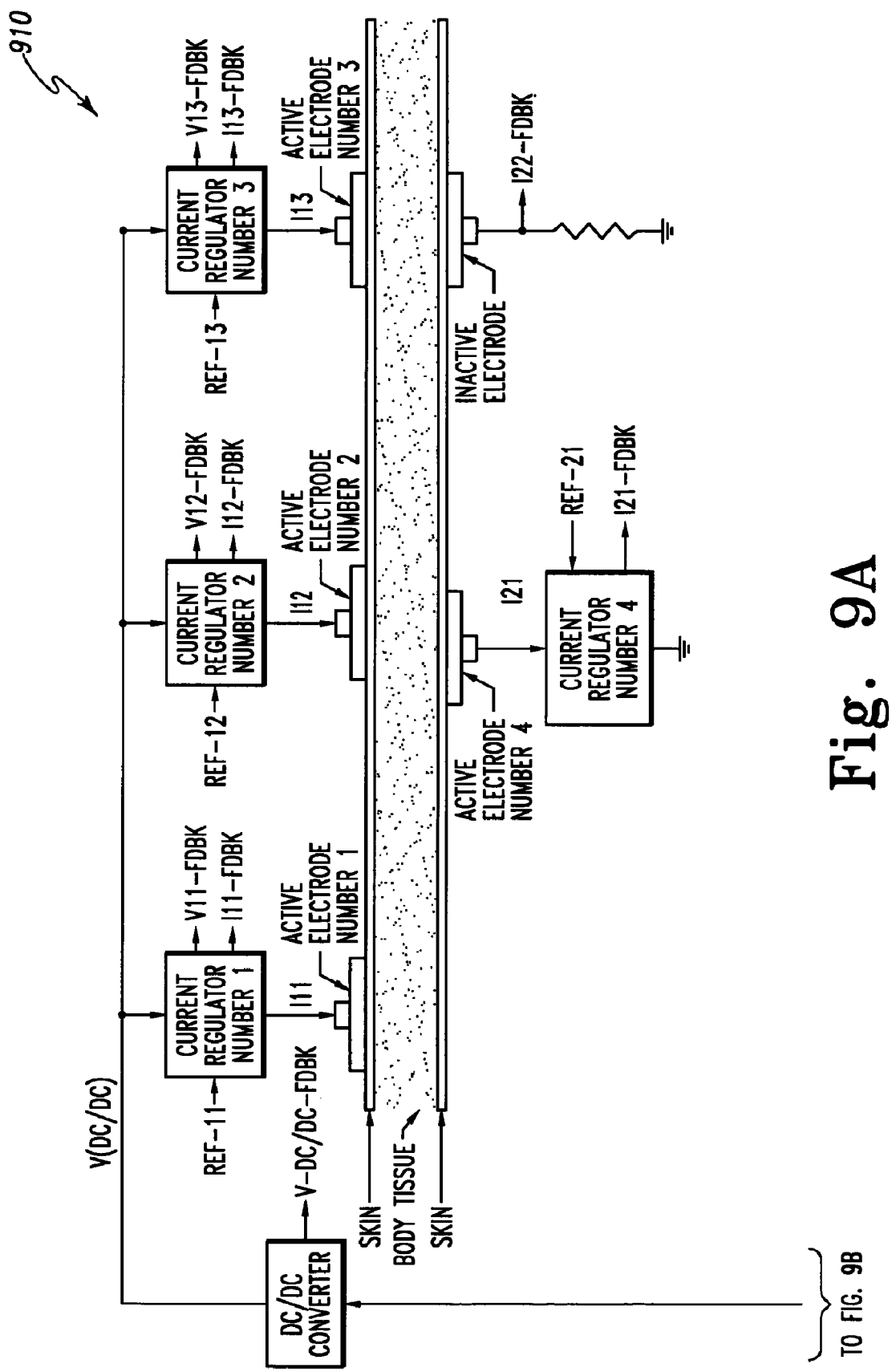
FIG. 9 is a simplified block diagram of a portion of an iontophoretic controller having simultaneous dual polarity operation.
Figure 9B:
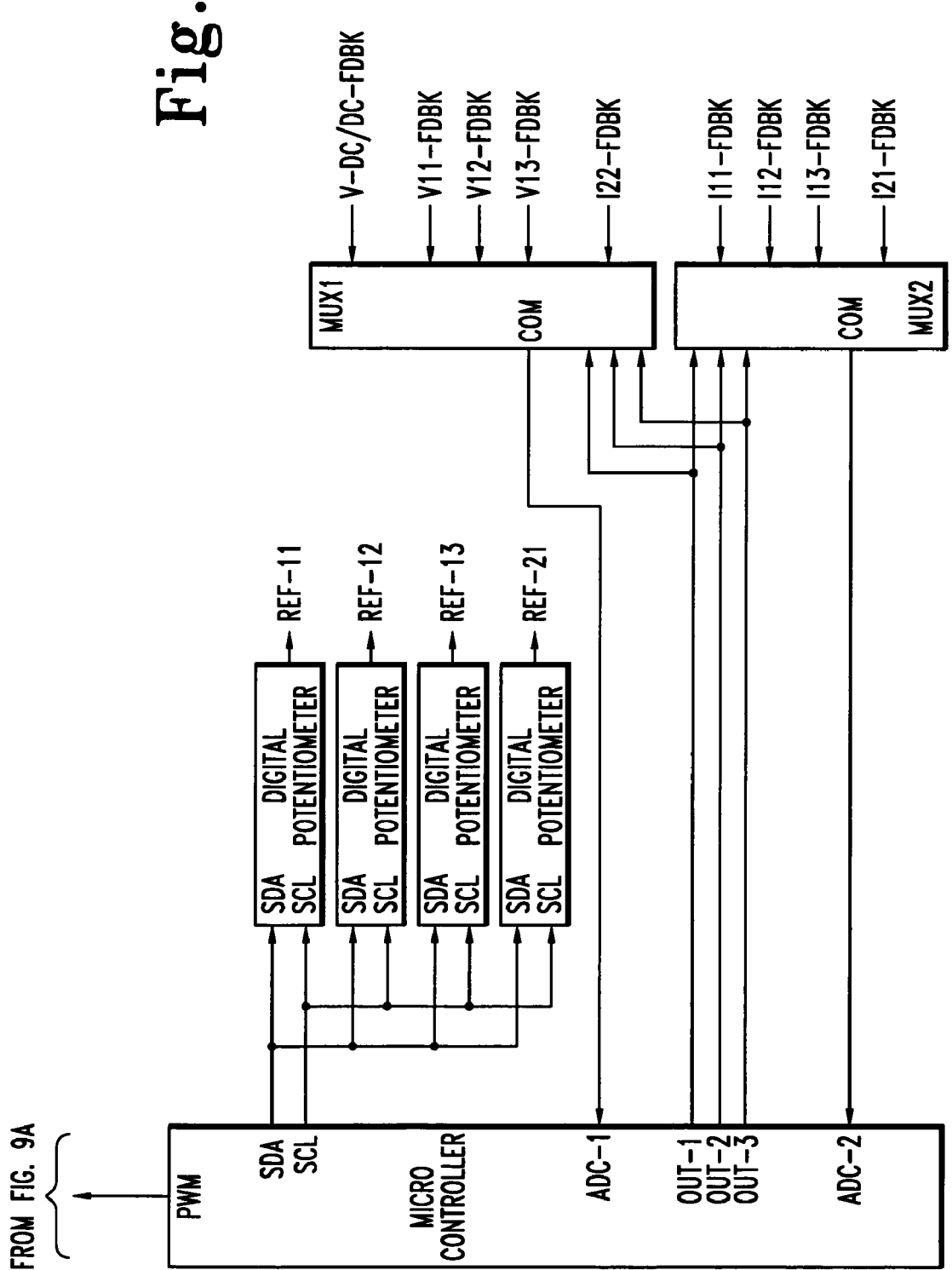

Turning to FIG. 9, a simplified block diagram is provided of circuitry for providing simultaneous dual polarity multi-channel current regulation. In the embodiment illustrated there are three positive drug active electrodes, one negative drug active electrode, and one inactive electrode. In accordance with this mode of operation there are one or more positive polarity current regulators and one or more negative polarity current regulators. In addition there are one or more current channels employing no electronic current regulator. Therefore there are three channels at minimum (i.e., one positive polarity current regulator, one negative polarity current regulator, and one virtual current regulator, which can be positive polarity or negative polarity).

Typically the number of required electronic regulators are one less than the number of electrodes. For example consider a 6-channel iontophoretic device that interfaces with 3 positive polarity drug active electrodes. There is no inactive electrode. There are three electronic positive polarity current regulators, which supply, for this example, a steady-state current of 2.0, 1.5, and 2.5 milliAmps respectively. The total current is 6.0 milliAmps. The three negative drug active electrodes require, for example, a steady-state current of 3.0, 2.0, and 1.0 milliAmps respectively. Two electronic negative polarity current regulators are employed to provide regulated currents of 1.0 and 2.0 milliAmps respectively. The remaining current is approximately 3.0 milliAmps. The reason six electronic regulators are not employed is due to the fact that regulators have a finite error (e.g., 1% accuracy), and as such placing electronic regulators in series may result in instability as one electronic regulator works against the other(s). The one non-electronic regulated channel is essentially regulated by virtue of the other electronic regulators. Consider for this example that all five electronic current regulators are +/−2% accurate, and assume the absolute worse case wherein the 3 electronic positive polarity current regulators provide 102% desired current (i.e., 6.12 milliAmps total in lieu of 6 milliAmps) and the two electronic negative polarity regulators provide 98% desired current (i.e., 2.94 milliAmps subtotal in lieu of 3 milliAmps). The remaining current will be 3.18 milliAmps (6.12-2.94), which is 6% high, which is acceptable for this example. The remaining current is controlled via the "virtual current regulator".

It should be noted that the accuracy of the virtual regulator is established in proportion to the accuracy of the other electronically regulated channels. Moreover, the feedback is obtained from all the channels (i.e., feedback is obtained from the one non-electronically regulated channel as well as the five electronically regulated channel) as may be required for functionality, safety, and regulation.

In addition, for another example, multiple unregulated current channels can be employed in lieu of one virtually regulated current channel. In this case although the total current for all of the unregulated channels is virtually regulated, the current in each individual channel is unregulated.

Turning to FIG. 10, a table is provided that outlines the desired specifications for an iontophoretic device with multiple electronic positive polarity current regulators only or multiple electronic negative polarity current regulators only. In the specifications, the device has no electronic regulators for the opposite polarity. Moreover, there will be one virtual regulated channel for the opposite polarity if one opposite polarity channel is utilized. Further, if more than one channel of the opposite polarity is utilized then these channels are unregulated.

Turning to FIG. 11, a table is provided that outlines the desired specifications for an iontophoretic device with non-simultaneous dual polarity operation, and with multiple positive polarity current regulators and multiple negative polarity current regulators. In the specifications, the device has no enabled electronic regulators for the opposite polarity. Moreover, there will be one virtual regulated channel for the opposite polarity if one opposite polarity channel is utilized. Further, if more than one channel of the opposite polarity is utilized then these channels are unregulated.

Turning to FIG. 12, a table is provided that outlines the desired specifications for an iontophoretic device with simultaneous dual polarity operation, and with one or more positive polarity current regulators, one or more electronic negative polarity current regulators, and one or more non-electronic current regulated negative polarity channels of current. In the specification, the negative polarity current channels may consist of a combination of either [1] one or more electronic current regulators and one virtual current regulator, or [2] one or more electronic current regulators and two or more unregulated channels of current.

Figures 13, 14:
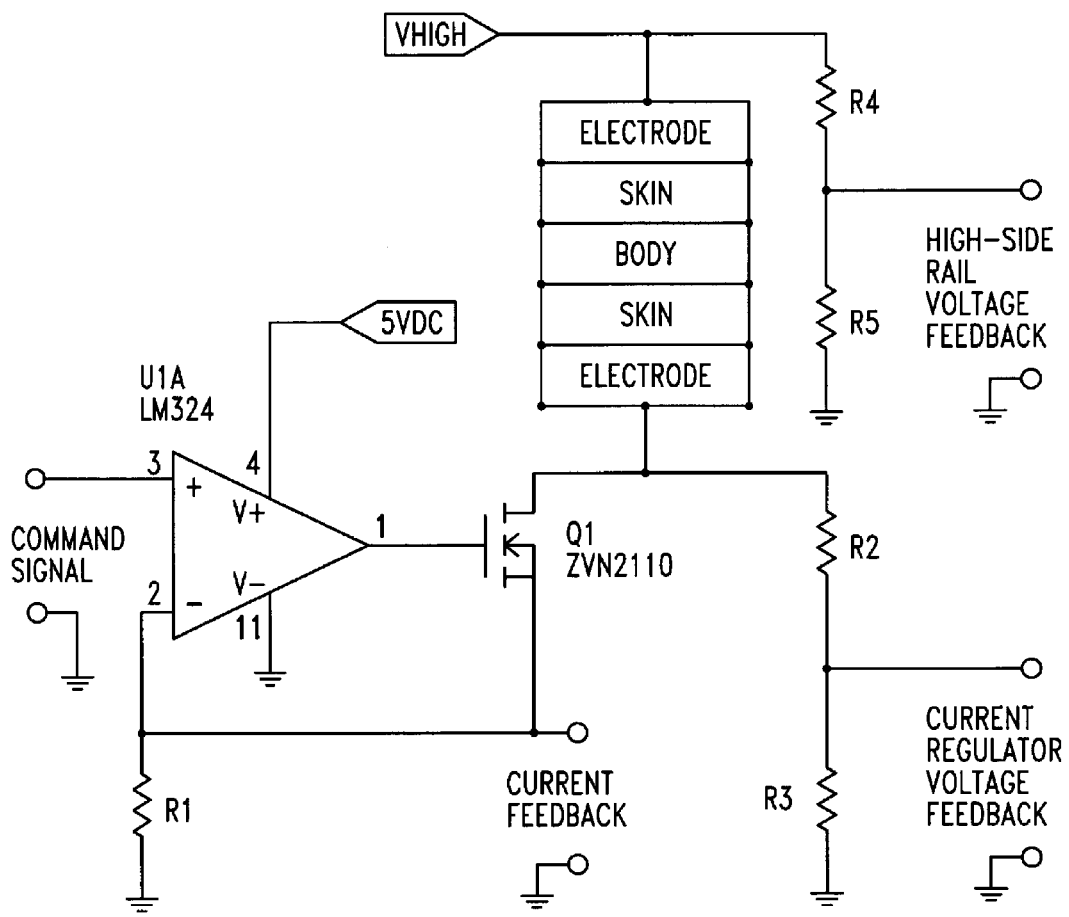
FIG. 13 is a table with desired characteristics of a dual polarity, simultaneous operation, non-electronic positive current channel(s)
FIG. 14 is a simplified schematic diagram of an alternate feedback circuit.

Turning to FIG. 13, a table is provided that outlines the desired specifications for an iontophoretic device with simultaneous dual polarity operation, and with one or more positive polarity current regulators, one or more electronic negative polarity current regulators, and one or more non-electronic current regulated positive polarity channels of current. In the specification, the positive polarity current channels may consist of a combination of either [1] one or more electronic current regulators and one virtual current regulator, or [2] one or more electronic current regulators and two or more unregulated channels of current.

In the above described devices, a channel is electronically regulated, virtually regulated, or unregulated. Any channel can be utilized in conjunction with either an active electrode or inactive electrode. Typically the current for each active electrode will be regulated. In certain applications the current for multiple inactive electrodes can be unregulated.

For example, consider a dual polarity device with simultaneous dual polarity operation, with three positive polarity channels and two negative polarity channels. The three positive polarity channels employ electronic current regulators. The two negative polarity channels employ one electronic current regulator and one virtual current regulator. The two negative channels are each connected to a negative drug electrode (i.e., to an active electrode). Two of the three positive channels are each connected to a positive drug electrode (i.e., to an active electrode). The remaining positive channel is connected to an inactive electrode. The current for the two positive drug electrodes is 3.0 mA and the current for the positive inactive electrode is 2.0 mA. Therefore the total positive current is 8.0 mA. The one electronically regulated channel of negative polarity current is 4.5 mA. Therefore the virtually regulated negative polarity current for the second negative electrode is 3.5 mA (i.e., 8.0-4.5).

Turning back to FIG. 6, it should be noted that the reference circuits (i.e., command signal circuits) are not limited to one D/A interfaced with multiple S/H Circuits via an Analog Multiplexer, as illustrated. For example multiple D/As, or multiple Digital Potentiometers, or similar reference circuits may be employed as illustrated in FIG. 9. In applications that mandate proportional tracking, i.e., in applications that do not mandate independently controlled command signals, a single D/A current regulator can be used to provide one command signal to all the current regulators as illustrated in FIG. 8. The current regulator outputs can be scaled equally (all currents are equal in magnitude) or scaled non-equally (all currents track proportionally but may vary in magnitude).

In FIG. 8, the buffer circuits track the D/A wherein each buffer has a different gain. For example REF-11 (i.e., the command signal for the first current regulator) has a gain of 1.00, while REF-12 has a gain of 1.25, and REF-13 has a gain of 1.45. This means that each channel of current tracks the master command signal from the D/A, but at a different proportional magnitude. For example, if Channel 1 provides a current of 1.0 milliAmp, then Channel 2 will provide a current of 1.25 milliAmps, and Channel 3 will provide a current of 1.45 milliAmps.

Turning back to the feedback circuits in FIGS. 6 and 8, these circuits employ analog multiplexers and a microcontroller with multiple analog inputs. Other feedback circuit options may be considered. For example multiple slave microcontrollers can be used in lieu of multiple multiplexers. Each microcontroller can monitor, and also control, one or two current regulators. The slave microcontrollers can then interface with a master microcontroller, via a serial bus, or the like.

Turning to FIG. 14 a low-side analog current regulator is illustrated. This circuit, by itself, is known in the prior-art and its operation is obvious to one skilled in the art. However, what is novel in the opinion of the invention is the use of this circuit for the methods described herein to facilitate the fabrication of multi-channel devices that are capable of providing multiple channels of negative polarity regulated current and/or multiple channels of positive polarity regulated current. A device having multiple channels of regulated negative polarity current as illustrated in FIG. 7.

Figure 15:
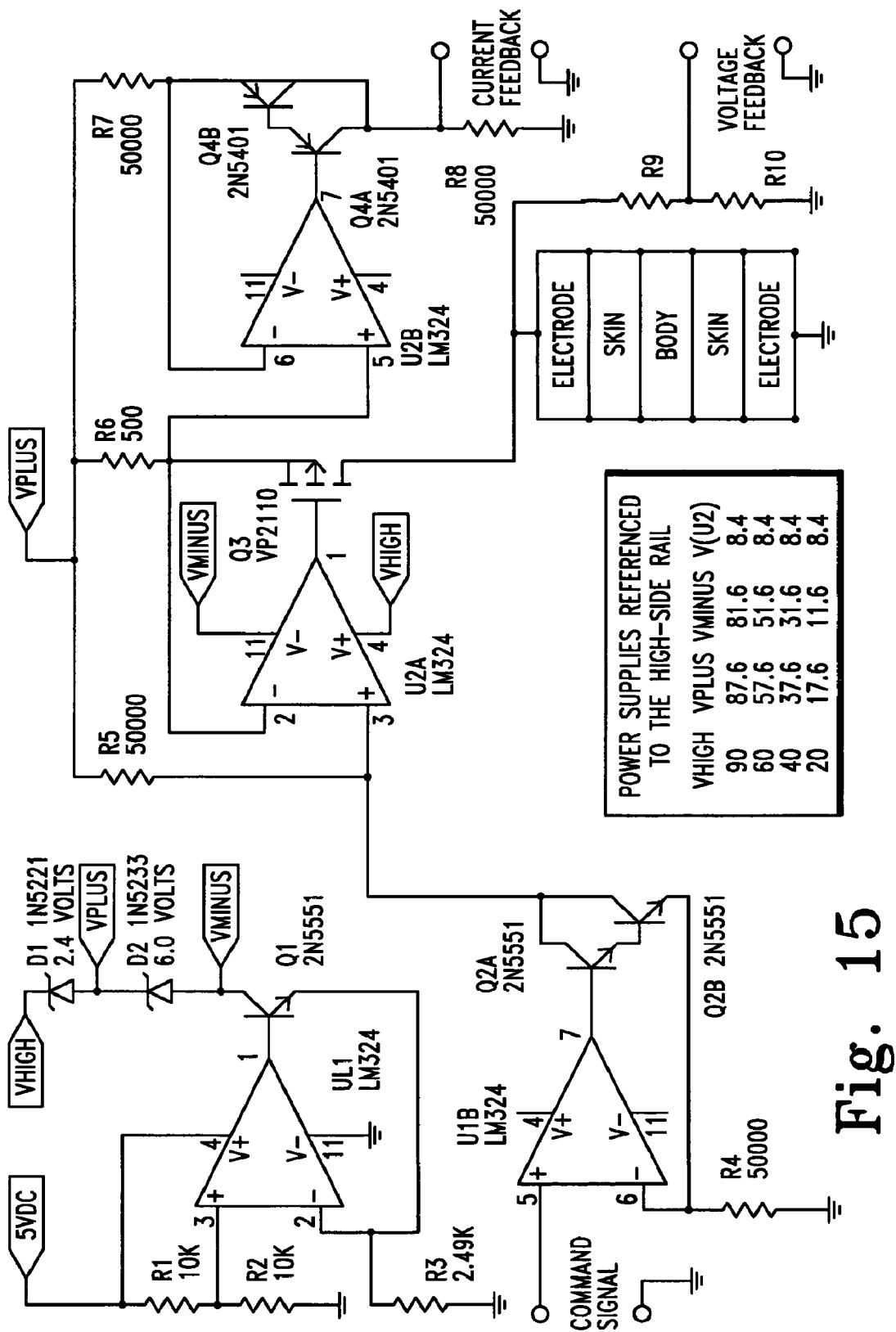
FIG. 15 is a simplified schematic diagram of a high-side current regulator suitable for use within an embodiment of the present invention.

FIG. 15 illustrates a high-side current regulator that operates in reference to the high-side rail (i.e., not in reference to power supply common rail). Some of the features of this circuit are [1] the current regulator circuitry (i.e., U2A and associated circuitry) is referenced to the high-side rail, [2] the command signal is referenced to the power supply common rail as required for interfacing with most standard microcontrollers, or similar control circuits, [3] the low-side command signal is converted to a high-side command signal as required by the current regulator circuitry, [4] the current feedback signal is referenced to the high-side rail, and [5] the high-side current feedback signal is converted to a low-side feedback signal, as required by most standard microcontrollers, or similar control circuits.

Figure 16:
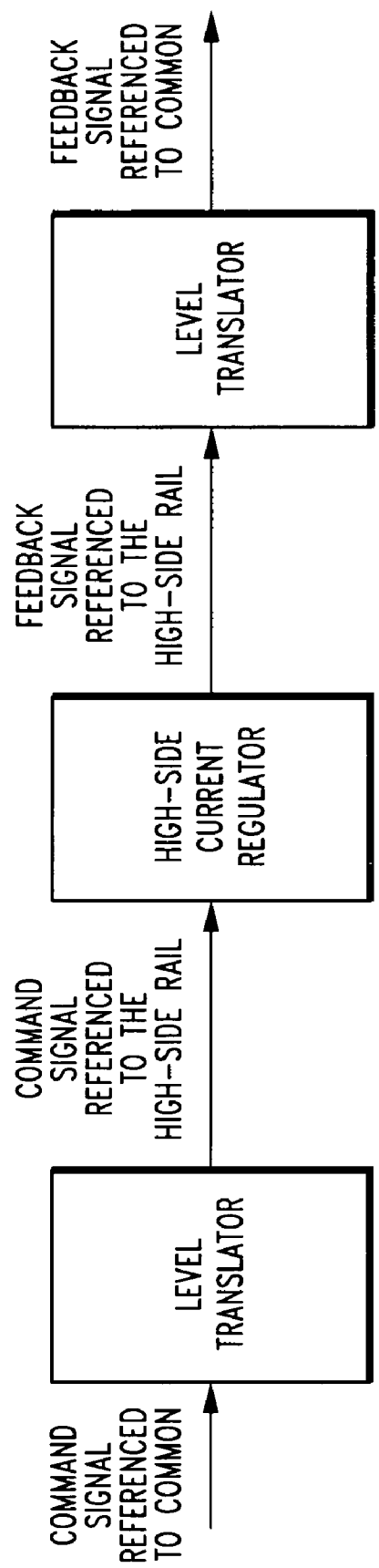
FIG. 16 is a simplified block diagram illustrating various transitions of an iontophoretic device in accordance with an embodiment of the present invention.

FIG. 16 is a block transformation that illustrates the translation of the input command signal from that which is referenced to the power supply common rail, and the translation of the output feedback signal to that which is referenced to the power supply common rail.

The operational amplifier U2A in FIG. 15 is low voltage device and also a low power device. The term "low voltage device", for this regulator circuit description, shall mean that the maximum power supply voltage specification of the operational amplifier (or equivalent servo mechanism) is less than the magnitude of the high-side power supply rail. In the illustrated example a very low cost and relatively low voltage operational amplifier (32 Volts maximum) is utilized in conjunction with a 90 Volt power supply high-side rail.

The operation of this circuit is somewhat analogous to the low-side current regulator illustrated in FIG. 14, however it is inverted, i.e., it is operating in reference to the high voltage power supply high-side rail in lieu of the power supply common rail. Like the low-side current regulator the command signal and the feedback signal of the high-side current regular are both referenced to the power supply common rail, via translator circuits. So this high-side current regulator device can interface with standard control and feedback circuitry (e.g., microcontrollers, DACs, ADCs, etc.) that are referenced to the power supply common rail. As such multiple circuits based on this high-side current regulator design can be employed in a manner analogous to the use of multiple low-side analog current regulators described above, as required to implement a device with multiple channels of regulated positive polarity current as illustrated in FIG. 6.

One of the advantages of the high-side current regulator is that each current regulator (i.e., each channel in a multi-channel device) can be constructed using a relatively small quantity of low cost components. This obviates the need for conventional high voltage amplifiers, or equivalent components, which are relatively expensive. Consider an example for an implementation requiring a 90 Volt current source.

In addition to the high cost of conventional high voltage amplifiers, high voltage amplifiers also require relatively large operating currents, which may render them unsuitable for battery powered applications (or other low power applications). This is not the case for the high-side current regulator illustrated. In addition conventional high voltage amplifiers typically require bipolar power supplies; again this is not the case for the high-side current regulator illustrated.

Turning back to FIG. 15, the LM324 depicted therein has a typical operating current of 0.7 mA. The circuit of U1A provides the power supply voltages for the high-side regulator. The high-side regulator and the differential amplifier for the current feedback employ two of the four amplifiers within one LM324 (U2A and U2B). Note that the remaining two (U2C and U2D) can be used for the second channel, assuming a multi-channel device.

The circuit of U1A sinks approximately 1 milliAmp through zener diodes D1 and D2 to provide the power supply voltages for U2. The difference of 0.3 milliAmp (i.e., 1.0-0.7) is sufficient to bias D2 into the required zener region.

For example a device that employs a DC/DC Converter that provides a voltage ranging from 15 Volts minimum to 90 Volts maximum. For instance a device with two channels of regulation (U2A-U2B are used for Channel 1 and U2C-U2D are used for Channel 2). The voltage is adjusted in proportion to the load resistance. If the device is used as an iontophoretic drug delivery controller/power supply, then the load (i.e., load resistance) is the sum total of the electrode effective resistances and skin-body effective resistance. Assuming the regulated current for each of the two channels is 4.0 mA and the load is 10 kOhm for the first channel and 12 kOhm for the second channel, then the required voltage is 40 Volts (V=I×R or 40=0.004×10,000) for the first channel and 48 Volts for the second channel. The second channel has the highest demand, and therefore establishes the required voltage. The DC/DC converter will typically be adjusted to 58 Volts to provide the required 48 Volts for the output and an additional 10 Volts to provide the required operating voltage for zener diodes, transistors (e.g., Q3), and resistors (e.g., R6), and also to provide a reserve voltage for typical small fluctuations in the load. Typically the DC/DC Converter voltage will be automatically readjusted every few milliseconds, based on the voltage feedback signals.

Zener diodes D1 and D2 provide a relatively stable voltage supply, which is derived from the voltage generated by the DC/DC Converter (i.e., is derived from the high-side rail). The high-side rail is designated "VHIGH" in FIG. 15. Diode D1 is a 2.4 Volt zener, and therefore power supply rail "VPLUS" is equal to VHIGH minus 2.4. Diode D2 is a 6.0 Volt zener, and therefore power supply rail "VMINUS" is equal to VHIGH minus 8.4. Consider an example wherein VHIGH=58 Volts, then VPLUS will equal approximately 55.6 Volts and VMINUS will equal approximately 49.6 Volts and VMINUS will equal approximately 41.6 Volts. Note that the power supply voltage for U2 will be approximately 8.4 Volts, regardless of the change in magnitude of high-side rail with respect to the power supply common rail. The positive power supply rail VPLUS is a few volts less than VHIGH. This is required because the LM324 cannot operate up to its own positive power supply voltage. The requirements for this offset will vary depending on the operational amplifier utilized. If additional channels are required then the sink current through Q1 can be revised accordingly. For example of four channels are required, this will require 2 LM324s (i.e., 8 operational amplifiers) and the Q1 sink current should be revised from 1.0 milliAmp to 1.7 milliAmp accordingly.

The circuit of U1B is the low-side to high-side command signal translator. For example consider an output requirement of 4.0 mA. A 2.0 Volt command signal is applied to U1B (at Pin 5). This forces a current of 0.04 milliAmp through the Darlington transistor configuration of Q2A-Q2B, which in-turn forces 0.04 milliAmp through resistor R5, which produces a 2.0 Volt command signal to U2A (at Pin 3). The Q2 Darlington transistor configuration is employed to minimize the error created by transistor base current. In lieu of this Darlington transistor configuration, a discrete Darlington transistor can be employed or a N-Channel MOSFET can be employed. (Note that a N-Channel MOSFET is preferred over the Darlington transistor configuration, however the N-Channel MOSFET is typically more expensive).

The 2.0 Volt command signal to U2A provides a 4.0 milliAmp current through R6 and therefore a 4.0 milliAmp output (through the body, i.e., through the load). If the load resistance exceeds a given maximum, then the circuit of U2A will provide less than 4.0 milliAmp. The decrease in output current will be in proportion to the increase in load resistance. The decrease in current will also occur through R6 as required for correct feedback monitoring. A bipolar transistor or bipolar Darlington transistor cannot be used for Q3, because as the load resistance increases beyond the maximum for a given current, the current will decrease in the output, but not decrease through R6 because Q3 will not be operating in its linear region. Thus a feedback signal based on the current through R6 because Q3 will be not be operating in its linear region. Thus a feedback signal based on the current through R6 will be invalid. Therefore the P-Channel MOSFET is employed for Q3, in lieu of a bipolar Darlington transistor configuration.

The circuit of U2B provides current magnitude feedback. If the output current is 4.0 milliAmp, then the voltage across R6 will be 2.0 Volts. Likewise the voltage across R7 will be 2.0 Volts, which will generate a current of 0.04 milliAmp through Darlington transistor configuration Q4A-Q4B. Again a Darlington transistor configuration is used to reduce the error created by the transistor base current, yielding transistor collector current approximately equal to the transistor emitter current as required. The 0.04 milliAmp current through resistor R8 provides the feedback signal of 2.0 Volts, which equates to 4.0 milliAmp. (Note again that a P-Channel MOSFET is preferred over the Darlington transistor configuration, however the P-Channel MOSFET is typically more expensive).

Voltage feedback is provided via the resistor divider circuit of R9 and R10. For example consider a maximum voltage of 90 Volts and an 8-Bit ADC with a voltage reference of 5.00 Volts, which equates to a resolution of 19.4 mV/LSB. The resistor attenuation ratio for R9 and R10 can be set to provide 4.844 Volts at 90 Volts, i.e., to provide a feedback signal of 48.44 millivolts per Volt, which equates to 0.4 Volts/LSB of feedback, which is satisfactory for this type of application.

Likewise similar voltage attenuators can be used to measure and monitor VPLUS, VMINUS, and VHIGH. If VPLUS and VMINUS are monitored, then additionally the sink current provided by U1A can be automatically controlled by the microcontroller (as required to optimize VPLUS and VMINUS), rather then employing a fixed 1.0 milliAmp sink current via the resistor ration of resistors R1 and R2) as indicated in FIG. 15). The advantage of this feature is that the sink current can be corrected for variances in the operating current for each of the operational amplifiers employed. Likewise if these voltages cannot be optimized and/or are incorrect, then an error message can be issued and the device operation can be prohibited accordingly.

The command translation circuitry of U1B can be used to drive multiple high-side regulators, if tracking is desired. This tracking can be setup to provide equal currents, or non-equal proportional currents.

If required, each current feedback resistor (e.g., R8) can be buffered using one of the operational amplifiers within a LM324 that is operating off the power supply common rail.

Moreover, if required, each voltage feedback resistor (e.g., R9) can be buffered using one of the operational amplifiers within a LM324 operating off of the power supply common rail.

The high-side current regulator embodiment just described may be used to implement an iontophoretic controller/power supply with one or multiple channels of regulated positive polarity current. Each channel may be independently controlled to provide independent currents or all the channels may be controlled proportionally to provide equal currents or proportional currents, or control may be a combination of one or ore independent channels and two or more tracking channels. The tracking feature is illustrated in FIG. 6 and is explained in the associated paragraph describing tracking.

One or more high-side current regulators can be used in combination with one or more low-side current regulators to implement a dual polarity device. As previously explained dual polarity operation may be simultaneous or non-simultaneous.

Non-simultaneous operation is illustrated in FIGS. 7 and 8 for low-side operation (i.e., single or multiple negative polarity current regulators) or FIGS. 5 and 8 for high-side operation (i.e., single or multiple positive polarity current regulators).

Figure 17:
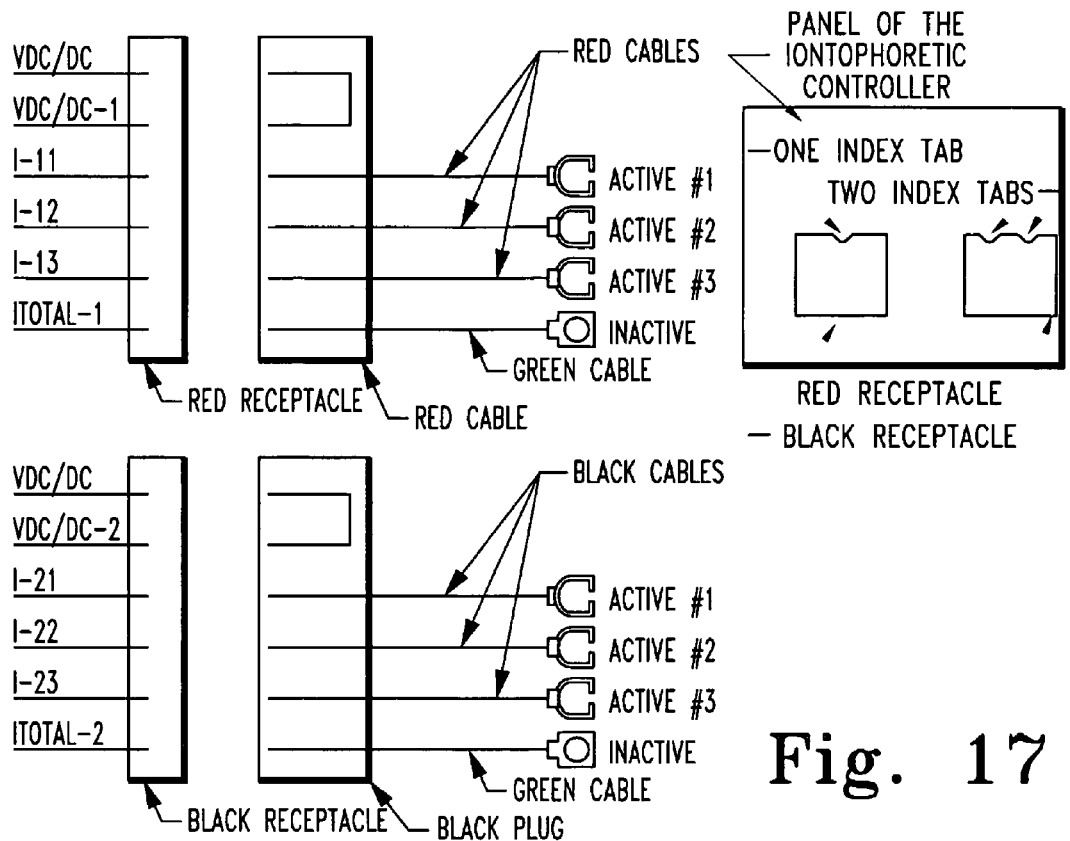
FIG. 17 is simplified electrode interface diagram for separate indexed polarity cable receptacles.

Turning to FIG. 17, illustrated therein is the electrode interface for a multiple-channel dual polarity iontophoretic device in accordance with the present invention. This embodiment is for a particular example comprising an iontophoretic device designed to provide either 3 channels of positive regulated current or 3 channels of negative regulated current in conjunction with one inactive electrode (i.e., non-simultaneous dual polarity operation). There are two types of cable assemblies: a cable assembly with 3 positive independent leads and one negative lead, and another cable assembly with 3 negative independent leads and one positive lead. The plugs, cables, and mating receptacles are indexed and color-coded to avoid the accidental insertion into the wrong receptacle. The plugs also include the High Voltage Switch illustrated in FIGS. 6 and 7. For example when the multi-positive cable assembly plug is inserted into the associated mating receptacle then node VDC/DC is connected to node NDC/DC-1, which in turn provides power to the positive polarity regulators (optional electronic circuitry can be added to detect the unacceptable case wherein both plugs are inserted simultaneously).

In this embodiment the cable assemblies are reusable. Each independent lead is terminated with an alligator snap, or circular spring-clip snap, or similar commercially available medical grade electrode connector, which in turn connects to a disposable active electrode or inactive electrode.

Figure 18:
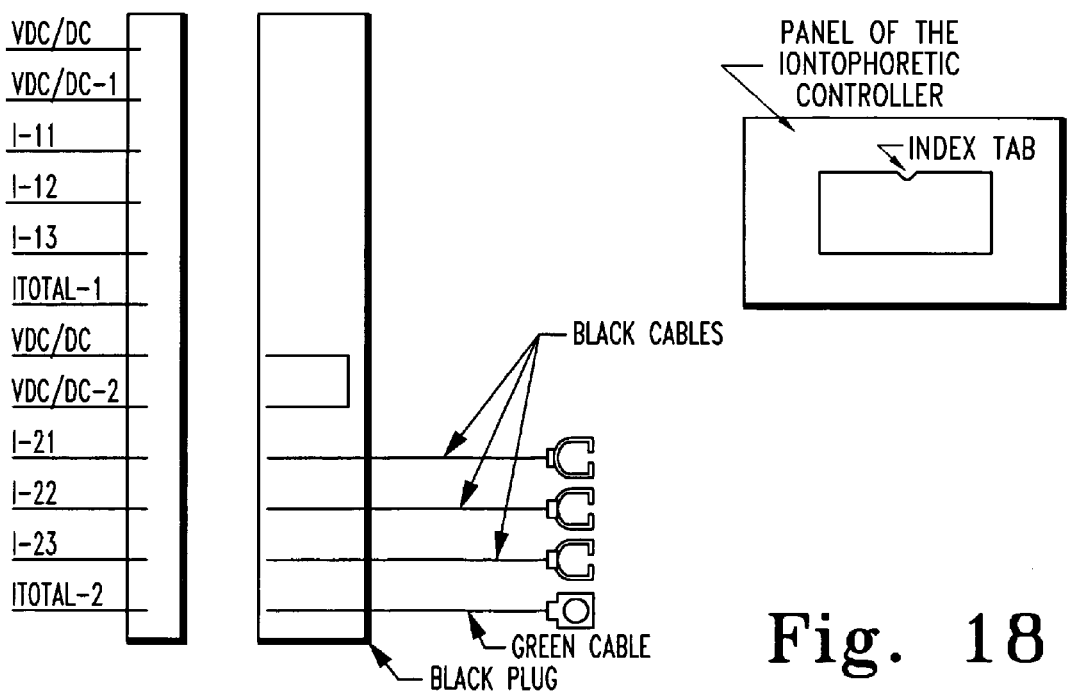
FIG. 18 is a simplified electrode interface diagram for common indexed polarity cable receptacles.

Another embodiment is illustrated in FIG. 18. In this embodiment there are again the two types of cable assemblies (multi-positive and multi-negative), however there is one universal receptacle. For example when the multi-negative cable assembly plug is inserted then node VDC/DC-2, which in turn provides power to the negative polarity regulators and simultaneously guarantees that no power is provided to the positive polarity regulators. As such this plug-receptacle feature guarantees that only one polarity can be utilized at one time, and like the previous embodiment the cables are color-coded to enhance the prevention of the accidental misuse of the wrong polarity.

Figure 19:
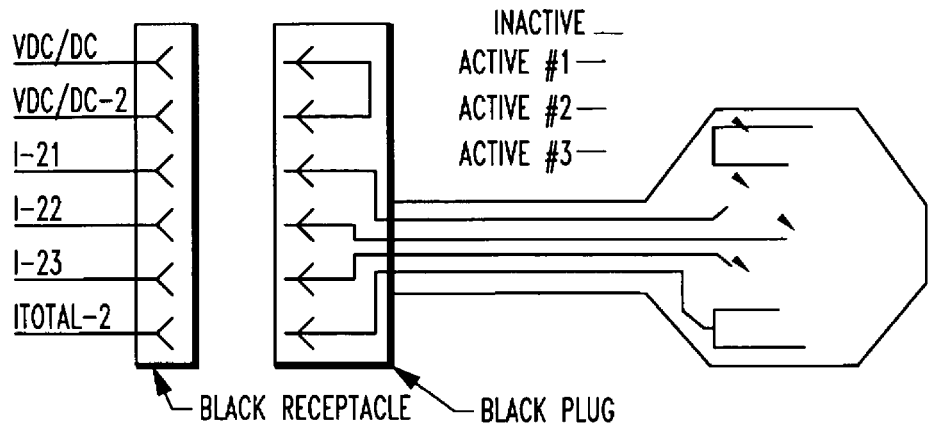
FIG. 19 is an embodiment of an electrode interface.

Based on presently available state-of-the-art technology, the plastic substrate used to manufacture the current distribution element of an iontophoretic electrode can be extended to include the interface ribbon-cable assembly that connects to the electronic iontophoretic device. This feature is illustrated in FIG. 19. This feature obviates the need for the reusable cable assembly with independent leads and eliminates the need to connect each electrode (or electrode segment) to each of the connectors at the termination of each of the independent leads in the previous examples. This feature becomes preferred in applications with large number of electrodes. Consider for example a facial iontophoretic electrode with 12 positive active electrode segments, 10 negative active electrode segments, and 4 inactive electrode segments. If a reusable cable assembly with independent leads is employed with this example application, then a great deal of time and effort is required to connect the 26 electrodes. In addition one can understand that the probability of an accidental mix-up of connections, or missing connections, or improper or loose connections, etc., increases as the number of electrodes increases.

Figure 20:
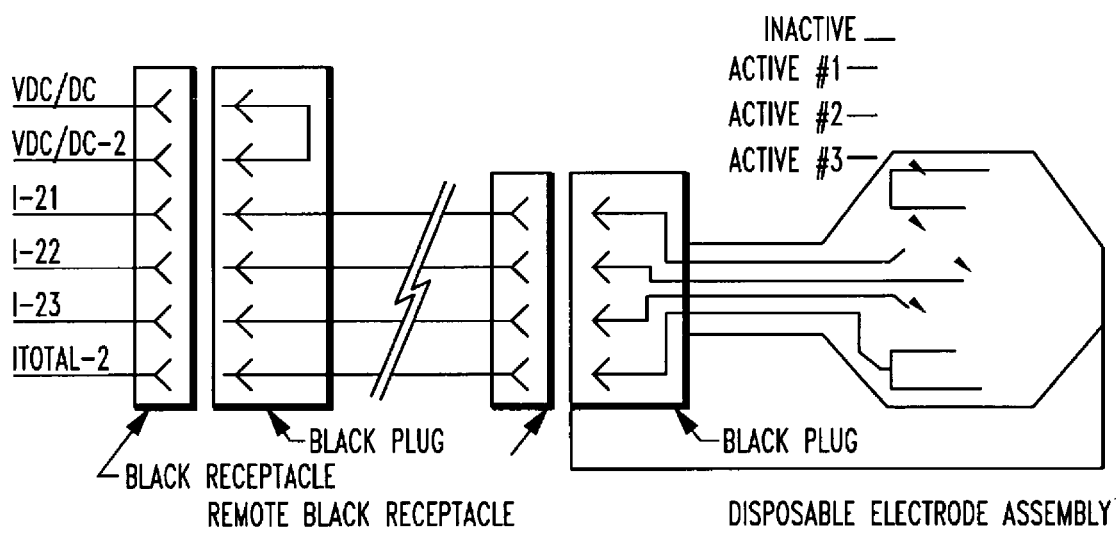
FIG. 20 is yet another embodiment of an electrode interface.

Turning to FIG. 20, a variant of the previous embodiment is depicted wherein a reusable extension ribbon-cable assembly is used in conjunction with a segmented electrode assembly that, like the previous ribbon-cable assembly embodiment, includes an integrated ribbon-cable assembly and connector. The advantage of this design over the previous embodiment is that the disposable integrated ribbon-cable assembly has a typical length of 36.0 inches while the ribbon-cable assembly of the disposable multi-segmented electrode has a length of only 2.0 inches, which, for this embodiment, yields an acceptable overall length of 38 inches.

In another example similar to that illustrated in FIG. 20, the extension ribbon-cable is hard-wired to the circuitry of the electronic iontophoretic device, thereby eliminating the receptacle and mating plug at the electronic device (as desired to reduce costs and/or simplify user operation and/or enhance reliability by reducing connector count and eliminating one connector).

It should be emphasized that the above-described embodiments of the present invention, particularly, and "preferred" embodiments, are possible examples of implementations merely set forth for a clear understanding of the principles of the invention. Many variations and modifications may be made to the above-described embodiment(s) of the invention without substantially departing from the spirit and principles of the invention. All such modifications are intended to be included herein within the scope of this disclosure and the present invention, and protected by the following claims.

What is claimed is:

1. An iontophoretic device comprising:
   an electrical channel having first and second sides;
   at least three electrodes, with at least two electrodes coupled to the first side and at least one electrode coupled to the second side, wherein each of the at least two first side electrodes electrically communicates with the at least one second side electrode;
   a controller that generates a control signal responsive to a first feedback signal indicative of current flowing through a first regulator and a second feedback signal indicative of current flowing through a second regulator, wherein each of the first and second regulators is coupled between an associated one of the at least three electrodes and the controller;
   a power source operatively connected to the controller and the first and second regulators; and,
   wherein, for each of the first and second regulators, a regulated current flows through both that regulator and its associated one electrode in response to the control signal.

2. The iontophoretic device of claim 1 wherein the power source is a converter.

3. The iontophoretic device of claim 2 wherein the power source is a DC/DC converter.

4. The iontophoretic device of claim 1 wherein the power source is coupled between the controller and an electrode.

5. The iontophoretic device of claim 1 wherein the power source is coupled between the controller and at least one of the regulators.

6. An iontophoretic device comprising:
a controller that generates a control signal responsive to a first feedback signal indicative of current flowing through a high-side regulator and a second feedback signal indicative of current flowing through a low-side regulator;
at least one high-side electrode associated with the high-side regulator;
at least one low-side electrode associated with the low-side regulator;
at least one additional electrode, wherein each additional electrode is one of a high-side electrode and a low-side electrode;
wherein each of the high-side regulator and the low-side regulator is operatively connected between its associated electrode on the corresponding side and the controller, and wherein, for each regulator, a current flows through both its associated electrode and that regulator in response to the control signal, and wherein the current flowing through the high-side regulator and the current flowing through the low-side regulator are not electrically isolated.

7. The iontophoretic device of claim 6 further comprising an electrode coupled to a current measurement device having a current feedback signal, and wherein the controller is responsive to the current feedback signal.

8. The iontophoretic device of claim 6 wherein the regulators have a current feedback signal and the controller is responsive to the current feedback signal.

9. The iontophoretic device of claim 6 wherein the regulators have a voltage feedback signal and the controller is responsive to the voltage feedback signal.

10. The iontophoretic device of claim 6 further comprising a power source operatively coupled to the controller and having a voltage feedback signal, and the controller is responsive to the voltage feedback signal.

11. The iontophoretic device of claim 10 wherein the power source is a converter.

12. The iontophoretic device of claim 11 wherein the converter is a DC/DC converter.

13. The iontophoretic device of claim 10 wherein the power source is operatively connected to the current regulators.

14. The iontophoretic device of claim 6 wherein the controller regulates the current flow in response to feedback signals from the current regulators, a power source, and a current measurement device.

15. The iontophoretic device of claim 6, wherein the at least one high-side regulator is non-simultaneously enabled with the at least one low-side regulator.

16. The iontophoretic device of claim 6, wherein the at least one high-side regulator is simultaneously enabled with the at least one low-side regulator.

17. An iontophoretic device comprising:
at least two low-side electrodes, wherein the at least two low-side electrodes are in electrical communication with a shared high-side electrode;
a controller that generates a control signal responsive to a first feedback signal indicative of current flowing through a first low-side regulator and a second feedback signal indicative of current flowing through a second low-side regulator, wherein each of the first and second low-side regulators is operatively connected between an associated one of the at least two low-side electrodes and the controller;
a power source operatively connected to the controller and the first and second low-side regulators; and,
wherein, for each of the first and second low-side regulators, a current flows through both that regulator and its associated one of the at least two low-side electrodes in response to the control signal.

18. The iontophoretic device of claim 17 further comprising an electrode coupled to a current measurement device having a current feedback signal, and wherein the controller is responsive to the current feedback signal.

19. The iontophoretic device of claim 17 wherein the regulators have a current feedback signal and the controller is responsive to the current feedback signal.

20. The iontophoretic device of claim 17 wherein the regulators have a voltage feedback signal and the controller is responsive to the voltage feedback signal.

21. The iontophoretic device of claim 17 further comprising a power source operatively coupled to the controller and having a voltage feedback signal, and the controller is responsive to the voltage feedback signal.

22. The iontophoretic device of claim 21 wherein the power source is a converter.

23. The iontophoretic device of claim 22 wherein the converter is a DC/DC converter.

24. The iontophoretic device of claim 17 wherein the controller regulates the current flow in response to feedback signals from the current regulators, a power source, and a current measurement device.

25. An iontophoretic device comprising:
a controller that generates a control signal responsive to a first feedback signal indicative of current flowing through a first high-side regulator and a second feedback signal indicative of current flowing through a second high-side regulator;
at least two high-side electrodes, wherein the at least two high-side electrodes are in electrical communication with a shared low-side electrode;
the two high-side regulators, wherein each regulator is operatively connected between an associated one of the at least two high-side electrodes and the controller;
a power source operatively connected to the controller and the high-side regulators; and,
wherein, for each regulator, a current flows through both its associated one of the at least two high-side electrodes and that regulator in response to the control signal.

26. The iontophoretic device of claim 25 further comprising an electrode coupled to a current measurement device having a current feedback signal, and wherein the controller is responsive to the current feedback signal.

27. The iontophoretic device of claim 25 wherein the regulators have a current feedback signal and the controller is responsive to the current feedback signal.

28. The iontophoretic device of claim 25 wherein the regulators have a voltage feedback signal and the controller is responsive to the voltage feedback signal.

29. The iontophoretic device of claim 25 further comprising a power source operatively coupled to the controller and having a voltage feedback signal, and the controller is responsive to the voltage feedback signal.

30. The iontophoretic device of claim 29 wherein the power source is a converter.

31. The iontophoretic device of claim 30 wherein the converter is a DC/DC converter.

32. The iontophoretic device of claim 25 wherein the controller regulates the current flow in response to feedback signals from the regulators, a voltage converter, and a current measurement device.

* * * * *